US011633489B2

(12) United States Patent
Thomsen et al.

(10) Patent No.: US 11,633,489 B2
(45) Date of Patent: *Apr. 25, 2023

(54) IRON CARBOHYDRATE COMPLEX FOR TREATMENT OF IRON DEFICIENCY OF A FETUS OR AN INFANT

(71) Applicant: PHARMACOSMOS HOLDING A/S, Holbaek (DK)

(72) Inventors: Lars Lykke Thomsen, Holte (DK); Tobias S. Christensen, Copenhagen S (DK); Hans Andreasen, Holbaek (DK)

(73) Assignee: PHARMACOSMOS HOLDING A/S, Holbaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/178,430

(22) Filed: Feb. 18, 2021

(65) Prior Publication Data

US 2021/0268118 A1 Sep. 2, 2021

Related U.S. Application Data

(62) Division of application No. 15/572,382, filed as application No. PCT/DK2016/050216 on Jun. 22, 2016, now Pat. No. 10,960,081.

(30) Foreign Application Priority Data

Jun. 22, 2015 (DK) .......................... PA 2015 70380

(51) Int. Cl.
*A61K 47/61* (2017.01)
*A61K 33/26* (2006.01)
*A61P 3/02* (2006.01)

(52) U.S. Cl.
CPC .............. *A61K 47/61* (2017.08); *A61K 33/26* (2013.01); *A61P 3/02* (2018.01)

(58) Field of Classification Search
None
See application file for complete search history.

(56) References Cited

U.S. PATENT DOCUMENTS

| 2009/0142360 A1 | 6/2009 | Connor et al. |
| 2012/0010166 A1 | 1/2012 | Andreasen |
| 2014/0099381 A1 | 4/2014 | Helenek et al. |

FOREIGN PATENT DOCUMENTS

| EP | 2913054 A1 | 9/2015 |
| JP | 2012521369 | 9/2012 |
| WO | 2006099237 | 9/2006 |
| WO | WO-2006/099237 A1 | 9/2006 |
| WO | WO-2009/120168 A1 | 10/2009 |

OTHER PUBLICATIONS

Milman, Journal of Pregnancy, vol. 2012, Article ID 514345, pp. 1-8. (Year: 2012).*
URMC, Health Encyclopedia, Iron and Total Iron-Binding Capacity-Online Medical Encyclopedia—University of Rochester Medical Center, internet article available Oct. 21, 2013. (Year: 2013).*
Pardridge, Journal of Cerebral Blood Flow & Metabolism (2012) 32, 1959-1972. (Year: 2012).*
International Search Report dated Sep. 28, 2016 issued in corresponding International Application No. PCT/DK2016/050216.
Danish Search Report dated Jan. 21, 2016 issued in corresponding Danish Application No. PA 2015 70380.
Scholl, Teresa O. "Iron status during pregnancy: setting the stage for mother and infant." *American Journal of Clinical Nutrition* 81 (2005): 1218S-1222S.
Lozoff, Betsy. "Iron deficiency and child development." *Food and Nutrition Bulletin* 28.4 (2007): S560-S571.
Lozoff, Betsy et al. "Functional Significance of Early-Life Iron Deficiency: Outcomes at 25 Years." *Journal of Pediatrics* 163.5 (2013): 1260-1266.
Lozoff, Betsy et al. "Iron Supplementation in Infancy Contributes to More Adaptive Behavior at 10 Years of Age." *Journal of Nutrition* 144 (2014): 838-845.
Bastian, Thomas W. et al. "Perinatal Iron and Copper Deficiencies Alter Neonatal Rat Circulating and Brain Thyroid Hormone Concentrations." *Endocrinology* 151.8 (2010): 4055-4065.
Monnot, Andrew D. et al. "Regulation of brain copper homeostasis by the brain barrier systems: Effects of Fe-overload and Fe-deficiency." *Toxicology and Applied Pharmacology* 256 (2011): 249-257.
Oladiji, Temidayo A. "Tissue levels of iron, copper, zinc and magnesium in iron deficient rats." *Biokemistri* 14 (2003): 75-81.
Myers, Stephen A. et al. "Zinc Transporters, Mechanisms of Action and Therapeutic Utility: Implications for Type 2 Diabetes Mellitus." *Journal of Nutrition and Metabolism* 2012 (2012): 1-13.
Zariwala, M. Gulrez et al. "A novel approach to oral iron delivery using ferrous sulphate loaded solid lipid nanoparticles." *International Journal of Pharmaceutics* (2013).
Jahn, Markus R. et al. "A comparative study of the physicochemical properties of iron isomaltoside 1000 (Monofer®), a new intravenous iron preparation and its clinical implications." *Journal of Pharmaceutics and Biopharmaceutics* 78 (2011): 480-491.
Toblli, J.E. et al. "Effects of iron deficiency anemia and its treatment with iron polymaltose complex in pregnant rats, their fetuses and placentas: Oxidative stress markers and pregnancy outcome." *Placenta* 33 (2012): 81-87.
Bingham, D. et al. "Increased transfer of iron to the fetus after total dose infusion of iron dextran during pregnancy." *Journal of Clinical Pathology* 36 (1983): 907-909.
Leuillet, M. and E. Salmon-Legagneur. "Sur l'utilisation d'un composé de fer dextrane hydrogéné (¹) par injection chez la truie en gestation et en lactation." *Annales de Zootechnie* 17.1 (1968): 59-70.

(Continued)

*Primary Examiner* — Layla D Berry
(74) *Attorney, Agent, or Firm* — Robin L. Teskin; Baker, Donelson, Bearman, Caldwell & Berkowitz PC (57) ABSTRACT

Disclosed herein is a pharmaceutical composition comprising an iron carbohydrate complex for use in a method for treatment or prevention of an iron deficiency of a fetus or an infant, wherein the iron carbohydrate complex is administered to the mother of the fetus or infant.

22 Claims, 4 Drawing Sheets

(56) References Cited

OTHER PUBLICATIONS

Myers, B. et al. "Comparative efficacy and safety of intravenous ferric carboxymaltose (Ferinject) and iron(III) hydroxide dextran (Cosmofer) in pregnancy." *Obstetric Medicine* 5 (2012): 105-107.
Seid, Melvin H. et al. "Ferric carboxymaltose injection in the treatment of postpartum iron deficiency anemia: a randomized controlled clinical trial." *American Journal of Obstetrics & Gynecology* 199.4 (2008): 435.e1-435.e7.
Unger, E.L. et al. "Effects of IV Iron Isomaltoside-1000 Treatment on Regional Brain Iron Status in an Iron-Deficient Animal." *Neuroscience* 246 (2013): 179-185.
Georgieff, Michael K. "The role of iron in neurodevelopment: fetal iron deficiency and the developing hippocampus." *Biochemical Society Transactions* 36 (2008): 1261-1271.
Molina, Ramon M. et al. "Ingestion of Mn and Pb by rats during and after pregnancy alters iron metabolism and behavior in offspring." *NeuroToxicology* 32 (2011): 413-422.
Milman N. "Iron in pregnancy—How do we secure an appropriate iron status in the mother and child?" Annals of Nutrition and Metabolism. 2011;59(1):50-4.
Milman N. "Oral iron prophylaxis in pregnancy: not too little and not too much!" J Pregnancy. 2012; 2012: 514345, pp. 1-8.
Chang et al. "Effect of iron deficiency anemia in pregnancy on child mental development in rural China." Pediatrics. Mar. 1, 2013;131(3):e755-63.
Holm C, et al. "Iron concentration in breast milk normalised within one week of a single high-dose infusion of iron isomaltoside in randomised controlled trial," Acta Paediatr. Feb. 2017;106(2):256-260.
Gambling, L et al. "Effect of iron deficiency on placental transfer of iron and expression of iron transport proteins in vivo and in vitro." The Biochemical journal vol. 356,Pt 3 (2001): 883-9. doi:10.1042/0264-6021:3560883.
Kumar, Ashok et al. "Cord blood and breast milk iron status in maternal anemia." Pediatrics vol. 121,3 (2008): e673-7. doi:10.1542/peds.2007-1986.
Aslam N, et al. "Experience with a novel intravenous iron preparation—Monofer in pregnant women with iron deficiency anaemia," Archives of Disease in Childhood—Fetal and Neonatal Edition 2014; 99:A148.
Khalafallah, Alhossain A, and Amanda E Dennis. "Iron deficiency anaemia in pregnancy and postpartum: pathophysiology and effect of oral versus inliavenous iron therapy." Journal of pregnancy vol. 2012 (2012): 630519. doi:10.1155/2012/630519.
Pavord, Sue et al. "UK guidelines on the management of iron deficiency in pregnancy." British journal of haematology vol. 156,5 (2012): 588-600. doi:10.1111/j.1365-2141.2011.09012.x.
Anonymous. "Monofer (iron) Infusion for Pregnant Women", Patient Information, May 2014 (2 pages).
Aslam et al. "PMM. 82 Experience with a novel intravenous iron preparation-Monofer in pregnant women with iron deficiency anaemia." Archives of Disease in Childhood-Fetal and Neonatal Edition. Jun. 1, 2014;99(Suppl 1):A148-.
Bingham et al. "Increased transfer of iron to the fetus after total dose infusion of iron dextran during pregnancy." Journal of clinical pathology. Aug. 1, 1983;36(8):907-9.
Holm et al. "Iron concentration in breast milk normalised within one week of a single high_dose infusion of iron isomaltoside in randomised controlled trial." Acta Paediatrica. Feb. 2017;106(2):256-60.
Khalafallah et al. "Iron deficiency anaemia in pregnancy and postpartum: pathophysiology and effect of oral versus intravenous iron therapy." Journal of pregnancy. Oct. 2012;2012.
Kwong et al. "Intein mediated hyper-production of authentic human basic fibroblast growth factor in *Escherichia coli*." Scientific reports. Sep. 22, 2016;6(1):1-9.
Leuillet et al. "Sur l'utilisation d'un composé de fer dextrane hydrogéné (1) par injection chez la truie en gestation et en lactation." InAnnales de zootechnie 1968 (vol. 17, No. 1, pp. 59-70).
Lozoff et al. "Iron deficiency and child development." Food and nutrition bulletin. Dec. 2007;28(4_suppl4):S560-71.
Myers et al. "Comparative efficacy and safety of intravenous ferric carboxymaltose (Ferinject) and iron (III) hydroxide dextran (Cosmofer) in pregnancy." Obstetric Medicine. Sep. 2012;5(3):105-7.
Pavord et al. "British Committee for Standards in Haematology. UK guidelines on the management of iron deficiency in pregnancy." British journal of haematology. Mar. 2012;156(5):588-600.
Toblli et al. "Effects of iron deficiency anemia and its treatment with iron polymaltose complex in pregnant rats, their fetuses and placentas: oxidative stress markers and pregnancy outcome." Placenta. Feb. 1, 2012;33(2):81-7.

\* cited by examiner

IRON CARBOHYDRATE COMPLEX FOR TREATMENT OF IRON DEFICIENCY OF A FETUS OR AN INFANT

CROSS REFERENCE TO RELATED APPLICATIONS

This application is a divisional of U.S. application Ser. No. 15/572,382, filed Nov. 7, 2017, now U.S. Pat. No. 10,960,081, which is a U.S. Nat'l Phase application of Intl Appl. No. PCT/DK2016/050216, filed Jun. 22, 2016, which claims priority to Danish Patent Application No. PA 2015 70380, filed Jun. 22, 2015, each of which is hereby incorporated by reference herein in its entirety.

FIELD OF THE INVENTION

The present invention relates to a pharmaceutical composition comprising an iron carbohydrate complex for use in a method for treatment or prevention of an iron deficiency of a fetus or an infant.

BACKGROUND

Maternal iron deficiency in the fertile age is a great challenge worldwide; for instance, in the developing countries an estimated 52% of pregnant females are anemic. In industrialised countries the prevalence of iron deficiency in e.g. female teenagers in the UK is 21%. It is therefore crucial to develop delivery strategies for pharmaceutical iron products to ensure sufficient levels of iron in the brain of the fetus.

Recent research has shown that many developing central nervous system (CNS) processes are highly dependent on iron-containing enzymes and proteins in essential functions like neurotransmitter synthesis and formation of myelin. The absence of sufficient supply of iron thus may result in an insufficient development of the brain. In the embryo, iron is furthermore thought to be essential for division of neurons and hence normal development of the CNS.

During pregnancy the demand for iron in both the mother and fetus increases, and iron deficiency anemia is most common late in pregnancy. In a study from USA, the frequency of iron deficiency anemia in the first, second and third trimesters were found to be 2%, 8% and 27%, respectively (Scholl et al., Am J Clin Nutr May 2005, vol. 81 no. 5, 1218S-1222S).

Betsy Lozoff describes in a background paper (*Food and Nutrition Bulletin*, vol. 28, n. 4, 2007, S560-S571) the effect of iron deficiency anemia on the developing brain. Studies on rodent models show that early iron deficiency directly affects oligodendrocytes, which form myelin, the fatty acid sheath around axons that helps speed neural transmission. Early iron deficiency also alters brain cell metabolism and morphology. Behavioral alterations in iron-deficient rats are consistent with the CNS effects. It was not possible by iron repletion beginning at weaning to reverse changes in the brain in gestation/lactation rodent models, which points to the importance of earlier intervention for iron deficiency.

Chronic iron deficiency in infancy has a long-term effect on the adulthood function, as disclosed in Betsy Lozoff, et al. *The journal of Pediatrics*, 2013. At 25 years 33 subjects with chronic iron deficiency in infancy were compared to 89 who were iron-sufficient before and after iron therapy. The results show that a high proportion of the group with chronic iron deficiency did not complete secondary school, were not pursuing further education or training, and were single. They reported poorer emotional health and more negative emotions and feelings of dissociation/detachment.

In a subsequent study Betsy Lozoff et al. The Journal of Nutrition 144:838-845, 2014, reports that iron supplementation in infancy contributes to more adaptive behavior at 10 years of age. Infants free of iron deficient anemia at age of 6 months were randomly assigned to iron supplementation or no added iron from age 6 to 12 months. At age 10 years, the group that received iron supplementation was more cooperative, confident, persistent after failure, coordinated, and direct and reality-oriented in speech, and working harder after praise compared with the no-added-iron group.

Iron deficiency also has an effect on the metabolism of other metals, i.e. zinc and copper (Bastian et al., Journal of Endocrinology, vol. 151, issue 8; Monnot et al., Toxicology and Applied Pharmacology, Volume 256, Issue 3, 1 Nov. 2011, Pages 249-257; Oladiji 2003, Biokemistri 14 (1): 75-81). Dysfunctional zinc-signaling is associated with serious conditions such as cardiovascular disease, diabetes, cancer and Alzheimer's disease (Myers et al., Journal of Nutrition and Metabolism Volume 2012 (2012), Article ID 173712, 13 pages). Furthermore, zinc functions as a co-factor for an estimated 3000 human proteins. Copper is also a co-factor for many proteins, among others, dopamine beta monooxygenase and superoxide dismutase—which are essential for the normal function of the CNS. Hence, any interruption in the metabolism of these metals is very serious.

While the importance of receiving iron for the embryo, fetus and the infant is established knowledge fetuses and infants still suffer from the iron deficiency anemia. Part of the problem is that orally administered iron has a low intestinal uptake; only 30-40% iron uptake was observed for 7 tested products in vitro in intestinal Caco-2 cells (Zariwala et al., International Journal of Pharmaceutics, Vol. 456, Issue 2, 18 Nov. 2013, Pages 400-407). When iron reaches the circulation of the pregnant female, it must cross the blood-placenta barrier to reach the circulation of the fetus. To reach the brain, the blood-brain barrier of the fetus is an additional challenge. As opposed to iron uptake in the gut—mainly carried out by the divalent metal transporter 1 (DMT1)— strictly controlled active transport is carried out at both the blood-placenta and the blood-brain barrier mediated by the transferrin receptor.

In vivo, the uptake is furthermore influenced by the composition of the diet, as the uptake of non-hem iron is increased by meat and ascorbic acid, but inhibited by polyphenols, phytates and calcium. Another part of the problem is that orally administered iron compositions not easily penetrate the blood brain barrier.

The present invention has the object of providing a pharmaceutical formulation for treatment of the mother in order to increase the iron content of the embryo, fetus or the infant.

BRIEF SUMMARY OF THE INVENTION

The present invention relates to a pharmaceutical composition comprising an iron carbohydrate complex for use in a method for treatment or prevention of an iron deficiency of a fetus or an infant, wherein the iron carbohydrate complex is administered to the mother of the fetus or infant.

It has surprisingly been found that iron from an iron carbohydrate complex administrated to a mother can pass the maternal blood-placenta barrier to the offspring.

In a preferred aspect of the invention the iron carbohydrate complex is parenterally administered to the mother of the fetus or infant. While the pharmaceutical composition of the present invention may be administered through various routes, including the oral administration route, the avoidance of the passage through the digestive tract of the mother generally improve the amount of available iron carbohydrate complex that can pass the maternal blood-placenta barrier.

In a preferred aspect of the invention the pharmaceutical composition according to the present invention is for use in a method for treatment or prevention of a disorder caused by brain metal deficiency. As shown herein the present inventors have surprisingly found that the iron from the iron carbohydrate complex can pass the fetus blood-brain-barrier to reach the brain of the fetus or infant. The treatment method may be used to cure or alleviate brain metal deficiency during infancy so that a lasting effect on the development during childhood can be avoided.

BRIEF DESCRIPTION OF THE SEVERAL VIEWS OF THE DRAWINGS

FIGS. 3A and 3B.

FIGS. 4A and 4B.

DETAILED DESCRIPTION OF THE INVENTION

The present invention relates to a pharmaceutical composition comprising an iron carbohydrate complex for use in a method for treatment or prevention of an iron deficiency of a fetus or an infant, wherein
the iron carbohydrate complex is administered to the mother of the fetus or infant.

It has surprisingly been found that iron from an iron carbohydrate complex administrated to a mother can pass the maternal blood-placenta barrier to the offspring.

In a preferred aspect of the invention the iron carbohydrate complex is parenterally administered to the mother of the fetus or infant. While the pharmaceutical composition of the present invention may be administered through various routes, including the oral administration route, the avoidance of the passage through the digestive tract of the mother generally improve the amount of available iron carbohydrate complex that can pass the maternal blood-placenta barrier.

In a preferred aspect of the invention the pharmaceutical composition according to the present invention is for use in a method for treatment or prevention of a disorder caused by brain metal deficiency. As shown herein the present inventors have surprisingly found that the iron from the iron carbohydrate complex can pass the fetus blood-brain-barrier to reach the brain of the fetus or infant. The treatment method may be used to cure or alleviate brain metal deficiency during infancy so that a lasting effect on the development during childhood can be avoided.

As used in the present context, the term "mother" covers all stages of becoming a mother having a child, including the period before fertilization, the pregnancy period, and the breastfeeding period.

The term "metal" as used in the present context covers trace metals such as iron, magnesium, lithium, zinc, copper, chromium, nickel, cobalt, vanadium, arsenic, molybdenum, manganese, selenium and others. Particularly important metals include iron, copper and zinc.

The term "disorder" covers any disturbance of the function of the physical or mental health, which is affected by brain metal deficiency. Specifically, brain iron deficiency affects neurotransmitters such as dopamine in brain and seems related to poor cognitive, motor, socialemotional or neurophysiologic development of the fetus or infant.

Specific particularly preferred disorders to be treated or prevented include restless leg syndrome (RLS), attention deficit hyperactivity disorder (ADHD), and attention deficit disorder (ADD). Preferred disorders to be treated or prevented include absence seizure, bipolar disorder, schizophrenia, obsessive-compulsive disorder (OCD), autism, and borderline personality disorder (BPD). Furthermore, it is anticipated that also other CNS diseases such as Alzheimer and Parkinson may be treated or prevented by the present invention.

The term "brain metal deficiency" covers detectable clinical deficiency of the metal as well as imbalance of the metal. Deficiency of the brain iron may result in imbalances of other metals in the fetal or infant brain. It is hypothesized that metal imbalances in the fetal or infant brain may lead to higher risk of CNS diseases in general. Examples of relevant metal imbalances include iron deficiency, copper deficiency, and increased levels of zinc.

The term "fetus" as used herein, covers any stage of development from the moment of conception to the moment of birth. Thus, the embryo is included in the term fetus.

"Infant" is intended to mean a child in the earliest period of life. Generally the infancy starts at birth and is ended around the age of 2 years. Thus, the infant stage includes the breastfeeding period.

The term "total dose" or similar expressions is intended to mean the total dose administrated a mother during each treatment course. A treatment course usually involves a single infusion or injection but may in certain circumstances be divided in two or more administrations. The duration of each treatment course is normally not above 5 days, such as not above 4, 3, or 2 days. Preferably, the treatment course is performed during a single day. According to the present invention a mother may be administrated two or more treatment courses prior to conception, during pregnancy, or during breastfeeding.

"Iron deficiency of a fetus or infant" is generally regarded to be present when blood levels of ferritin is less than 15-30 µg/L or when blood levels of ferritin are less than 100 µg/L in combination with transferrin saturation (TSAT) less than 20%. A fetus or infant may be regarded "brain iron deficient" when the magnetic resonance phase imaging is 0.02 radians above the average value of a control group in certain brain areas such as the substantia nigra, thalamus, putamen, or pallidum. The magnetic resonance phase imaging uses tissue magnetic susceptibility differences to generate a contrast different from that of the spin density, $T_1$, $T_2$, and $T_2^*$. T1 denotes the spin-lattice and T2 the spin-spin relaxation. The method is a sensitive tool to quantify cerebral iron content. It measures phase shift in the gradient-echo images, which, measured in radians, are inversely correlated with iron content. Tissue-containing paramagnetic iron exhibits a negative phase in complex images compared with immediate adjacent tissue, which will have an increased phase. A suitable apparatus is a 1.5 Tesla MR system.

Without being bound by theory, it is presently believed that iron or the iron carbohydrate complex is mainly entering the fetus brain at certain time slots during a day, i.e. the brain exerts a circadian variation in the absorption of iron or the iron carbohydrate complex. Therefore, it is according to this theory desirable to use iron carbohydrate complexes with longer pharmacokinetic half life because these complexes will remain for longer time in blood or plasma and thus present iron to the brain for a longer time period.

In a preferred aspect of the present invention the pharmacokinetic half life ($t_{1/2}$) of the iron carbohydrate complex is 10 hours or more to offer the brain a sufficient amount of iron during 24 hours. Suitably, the pharmacokinetic half life of the iron carbohydrate complex is 12 hours or more, such as 14 hours, 16 hours, 18 hours, 20 hours, 22 hours or more. However, the pharmacokinetic half life of the iron carbohydrate complex should not be too high, such as above 100 hours, e.g. the pharmacokinetic halflife should not be above 90 hours, such as 80 hours, 60 hours, or 40 hours, to ensure availability of iron. In certain embodiments of the inventions the pharmacokinetic half life may be lower, such as 9 hours, 8 hours, 7 hours, 6 hours, 5 hours, or more. If a low pharmacokinetic half life is chosen, it may be beneficial to deliver a dosage 2 or more times during a day. Each dosage administration should be distanced at least 4 hours from the previous administration. Example 4 shows pharmakokinetic data from six trials of Monofer®, which is a preferred iron carbohydrate complex The total dose of the iron carbohydrate complex may vary in dependency of e.g. the body weight or the age of the patient. Generally, the total dose of elemental iron from the iron carbohydrate complex administered to the mother is 300 mg elemental iron or more. To ensure a sufficient treatment of the mother for a long lasting effect on the offspring it is generally recommended that the total dose of elemental iron from the iron carbohydrate complex administered to the mother is 400 mg elemental iron or more, such as 500 mg, 600 mg, 700 mg, 800 mg, 900 mg, 1000 mg or more. The dose of elemental iron should not exceed 3000 mg to avoid iron overload.

The iron carbohydrate complex may be considered a vehicle for transportation of iron to the brain. Usually, the iron carbohydrate complex is selected from the group comprising iron carboxymaltose, iron polyglucose sorbitol carboxymethyl ether complex, iron dextran, iron hydrogenated dextran, iron gluco-oligosaccharides, iron reduced gluco-oligosaccharides, iron oxidated gluco-oligosaccharides, iron carboxyalkylated reduced oligo- and poly saccharides, iron dextrin, iron hydrogenated dextrin, iron polymaltose, iron hydrogenated polymaltose, iron polyisomaltose, iron hydrogenated polyisomaltose, iron oxidised dextrin, iron oxidised dextran, iron hydroxide adipate tartrate, iron polullan, iron hydrogenated polullan, iron oxygenated polullan, or mixtures thereof. In a preferred aspect, the iron reduced gluco-oligosaccharide is iron hydrogenated oligoisomaltoside.

The iron carbohydrate complex may originate from various sources and be processed in accordance with a multitude of methods. Some dextran types are suspected of being immunogenic and to be the reason for anaphylactic shock. It is believed that the reason for the immunogenic tendency observed for some types of dextrans is due to the presence of branches of glucose units linked to the backbone through α-1,3 glycosidic linkages. Thus, in an embodiment of the present invention the iron carbohydrate complex is iron hydrogenated dextran having a carbohydrate component comprising a backbone of glucose units linked by α-1,6 glycosidic linkages and optionally branches of glucose units linked to the backbone through α-1,3 glycosidic linkages, wherein the proportion of α-1,3 glycosidic linkages to α-1,6 glycosidic linkages is less than 5:100, such as less than 1:100. The low amount of branches of glucose units linked to the backbone through α-1,3 glycosidic linkages may have less tendency to provoke an immunological response to the treatment. In a preferred aspect of the invention the carbohydrate component does not comprise detectable branches of glucose units linked by α-1,3 glycosidic linkages to the backbone. According to the theory, the absence of detectable α-1,3 glycosidic linkages should avoid any immunological reaction due to antibodies raised in the body towards dextran or dextran-like molecules.

In a preferred embodiment of the invention, the iron carbohydrate complex is (1→6)-α-D-glucopyranan-(1→6)-D-glucitol iron(III) complex.

The iron carbohydrate complex may be produced with various lengths of the carbohydrate component. In a certain aspect the weight average molecular weight (MW) of the carbohydrate component of the iron carbohydrate complex is 800 to 40,000 Dalton, such as 800 to 10,000, and preferably 800 to 2,000 Dalton. In a preferred aspect of the invention, the weight average molecular weight of the carbohydrate component is around 1,000 MW. An iron carbohydrate complex prepared from this particular carbohydrate component has high storage stability as well as a suitable pharmacokinetic half life. Generally, the apparent molecular weight of the iron carbohydrate complex measured relative to dextran standards, is 400.000 Dalton or less, such as 300.000 Dalton or less, and preferably 200.000 Dalton or less. Generally, the apparent molecular weight of the iron carbohydrate complex is above 20.000 Daltons, such as above 50.000 Daltons, and preferably above 100.000 Daltons. The method of determining the apparent molecular weight using dextran standards is disclosed in Jahn M R, et al, European Journal of Pharmaceutics and Biopharmaceutics 78 (2011) 480-491.

The iron carbohydrate complex used in the present invention generally comprises one or more iron cores and a plurality of carbohydrates. The mean iron core size is suitably not greater than about 15 nm and usually in the range of at least about 1 nm to no greater than about 15 nm, such as at least about 3 nm but no greater than about 10 nm, and preferably at least about 5 nm but not greater than about 8 nm. The complex may contain any appropriate number of iron molecules per one carbohydrate, such as between 1 to 100 iron molecules per carbohydrate molecule, such as 5 to 50 or preferably 7 to 20 iron molecules per carbohydrate molecule. In a preferred aspect the iron carbohydrate complex comprises about 10±5 iron molecules per one carbohydrate.

The shell diameter measured by dynamic light scattering (DLS) includes the iron core as well as the carbohydrate shell. The medians of the hydrodynamic diameters are generally in the range of 5 to 50 nm, such as in the range of 7 to 30 nm. In an aspect of the invention the average size of the medians of the hydrodynamic diameters is about 10±5 nm.

In a preferred aspect of the invention the iron carbohydrate complex is Monofer®, an iron hydrogenated oligoisomaltoside having an apparent molecular weight of around 150,000 Daltons, an iron core of 5-8 nm, a shell diameter of around 10 nm, and about 8 iron atoms per carbohydrate molecule. The carbohydrate component has a weight average molecular weight of around 1,000 MW and comprises glucose units linked by α-1,6 glycosidic linkages without detectable branches of α-1,3 glucose units with a reduced end group.

According to an embodiment of the present invention, the pharmaceutical composition is a liquid formulation suitable for parenteral administration, such as injection or infusion, optionally after appropriately being diluted. In another aspect of the invention the pharmaceutical composition is a powder capable of being dissolved in a suitable liquid for the preparation of a medicament to be delivered parenterally to a human patient.

The iron carbohydrate complex may be intravenously administered in fairly high amounts, which offers the possibility to administer high iron doses in one visit over a short period of time for the benefit and convenience of patients and healthcare professionals. The total dosage used in the present invention may be administered as a single dosage or in multiple dosages. To increase the patient compliance and the general desire of effective treatment, it is generally desirable to deliver the iron carbohydrate complex in a single dosage. While the iron carbohydrate complex may be delivered in any suitable way, including a location outside the digestive tract, the liquid pharmaceutical composition is normally administered as an intravenous (iv) or intramuscular (im) injection or infusion. In a certain aspect, the pharmaceutical composition is intravenously infused into a mother during 3-30 min, such as 5 to 25 min, and preferable 10-20 min. In another aspect of the invention the pharmaceutical composition is infused into a mother during 16 to 30 min.

The appended experiments suggest that the iron carbohydrate complex may enter the fetus brain during the entire pregnancy period. Specifically, it has been shown that administration of the iron carbohydrate complex at the entry of the first and the third trimester of the pregnancy results in accumulation of iron in the brain. While the availability of iron is important for the fetus during the entire pregnancy period, it is especially important in the second and third trimester when the prefrontal cortex is developed.

In a certain aspect of the invention it may be advantageous that the iron carbohydrate complex is administered to the mother before conception. The administration of the iron carbohydrate complex to the soon to become mother builds up the iron stores primarily in the liver and ensures that circulating iron is available for the fetus at the early stages thereof. In an aspect of the invention the iron carbohydrate complex is administered to the mother one month or less before conception. In specific examples, the iron carbohydrate complex is administered to the mother 3 weeks, such as 2 weeks or 1 week before the conception.

It is anticipated that the iron carbohydrate complex administered parenterally to the mother or a conversion product thereof enters into the breast milk. Thus according to an embodiment of the present invention, the iron carbohydrate complex is administered to the mother after birth during the breastfeeding period.

Iron in breast milk is generally better absorbed than from other sources. It is believed that the vitamin C and the high lactose levels in breast milk aid in iron absorption. In an embodiment the iron carbohydrate complex is administered to the mother within 6 month after birth of the infant, such as within 5, 4, 3, 2, or 1 months after birth.

A first iron carbohydrate complex administered parenterally will be available for the absorption by the mother, the fetus, or the infant for a certain time period, which time period generally is dependent on the pharmacokinetic half life of the specific iron carbohydrate complex. In an embodiment of the invention the mother is subjected to a further administration of the iron carbohydrate complex during pregnancy or the breastfeeding period.

The further administration makes available to the mother, the fetus, or the infant another portion of the iron carbohydrate complex for replenish stores of iron. In an aspect of the invention the further administration is performed 1 week to 12 months after the previous administration.

The further administration can be performed one or more times, such as 2, 3, 4, 5, 6, 7, 8, 9, 10, or more times during the pre-conception, pregnancy, and breastfeeding period.

According to the present invention administration of the iron carbohydrate complex prevents or treats abnormal development of the fetal or infant brain. While the iron carbohydrate complex delivered to the fetus through the exchange in placenta and to the infant through the gastrointestinal tract is introduced into the fetus or the infant systemically, it has surprisingly been possible to target the brain, i.e. the iron from the iron carbohydrate complex is accumulated in the brain. Some areas of the brain appear more prone to absorb the iron from the iron carbohydrate complex. Thus according to the present invention administration of the iron carbohydrate complex prevents or treats abnormal development of the substantia nigra, thalamus, putamen, ventral midbrain, or pallidum.

A number of diseases or disorders are associated with brain iron deficiency. According to an aspect of the invention the iron carbohydrate complex administered to the mother supports cognitive, motor, social-emotional, or neurophysiologic development of the fetus or infant. Specific diseases or disorders to be treated or prevented include restless leg syndrome (RLS), attention deficit hyperactivity disorder (ADHD), attention deficit disorder (ADD), absence seizure, bipolar disorder, schizophrenia, obsessive-compulsive disorder (OCD), autism, and borderline personality disorder (BPD).

The administration of the iron carbohydrate complex to iron deficient rats has surprisingly shown a co-uptake of other metals, such as copper and zinc. Therefore, the present invention may find application in the treatment of disorders caused by other metals than iron. Examples of such metals include zinc and copper. It is however, anticipated that other trace metals may be co-absorbed as well.

Example 1

16 iron deficient female Wistar rats fed a low iron diet with an iron content of 5.2 mg/kg (Altromin, Ger) for six weeks were obtained from timed pregnant rats and randomly divided in two groups of 8. Group 1 rats was injected subcutaneously on the date of the conception with varying dosages of pharmaceutical composition comprising an iron carbohydrate complex (E0) and Group 2 rats received varying dosages 14 days after conception, i.e. at the entry of the third trimestre, of a pharmaceutical composition comprising an iron carbohydrate complex (E14).

Each of the groups 1 and 2 was divided into four sub-groups (A-D) of 2 mated female rats that received dosages of a pharmaceutical composition comprising the iron carbohydrate complex Iron isomatoside 1000 (Monofer®) as specified in the scheme:
A) 0 mg Fe/kg as Monofer®
B) 20 mgFe/kg as Monofer®
C) 40 mgFe/kg as Monofer®
D) 80 mgFe/kg as Monofer®

In addition a control group (K) of fertilized females was kept on iron-containing diet with an iron-content of 158 mg Fe/kg (Altromin, Ger) diet throughout the experiment.

At the time of birth (P0) the level of iron of 4 pups from each mother was measured in the brain. The rats were deeply anesthetized with a subcutaneous injection of 0.5 ml/10 g body weight of Hypnorm/Dormicum (Fentanyl/Fluanisone mixed with Midazolam). Subsequently, the chest was opened and blood sampled by heart puncture. The brain stem were then dissected and used for detection of the concentration of iron by Inductively Coupled Argon Plasma with Optical Emission Spectrometry detection (ICP-OES) (ICAP 6300 Duo View, Thermo Scientific). The data were pooled for each of the dosage levels and FIG. 1 shows the results.

Figure 1:
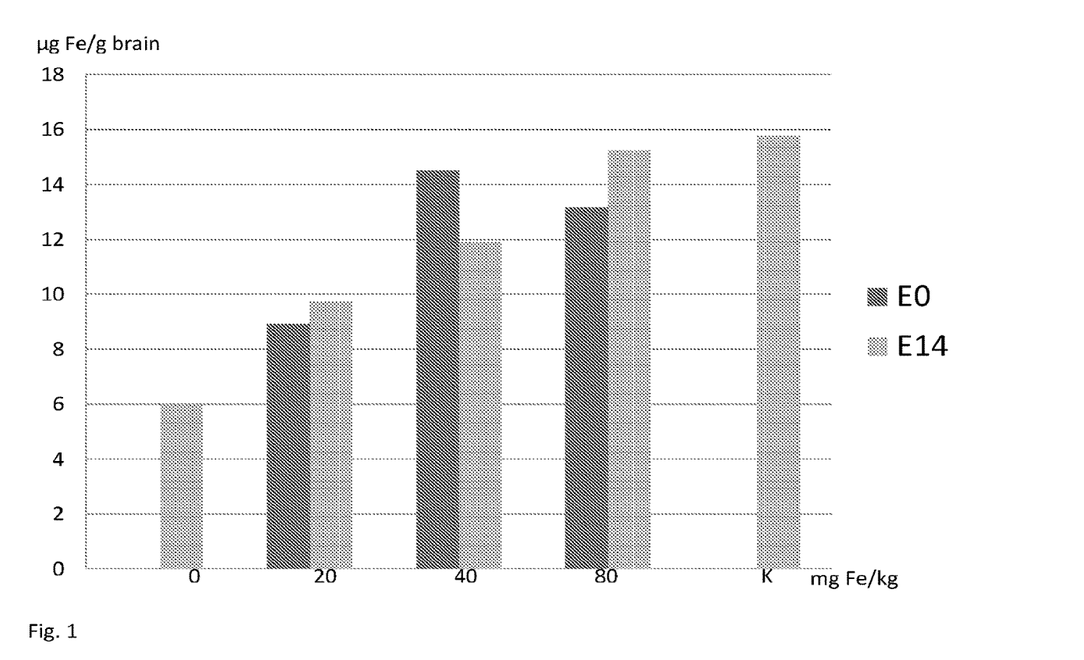
FIG. 1 shows a dosage-dependent relationship for brain iron when dosage levels ranging from 0 mg/kg to 80 mg Fe/kg are used. The dosage-dependent relationship for brain iron applies for the E0 group as well as the E14 group. No significant differences appear to be present between the E0 and the E14 groups, indicating that the iron carbohydrate complex is transferred relatively fast from the maternal blood through the placenta to the fetus blood and finally through the blood-brain-barrier into the brain vessel of the fetus. Furthermore it may be concluded that the iron carbohydrate complex remains in the brain, i.e. it is not reentering the blood stream.

FIG. 1 shows a dosage-dependent relationship for brain iron when dosage levels ranging from 0 mg/kg to 80 mg Fe/kg are used. The dosage-dependent relationship for brain iron applies for the E0 group as well as the E14 group. No significant differences appear to be present between the E0 and the E14 groups, indicating that the iron carbohydrate complex is transferred relatively fast from the maternal blood through the placenta to the fetus blood and finally through the blood-brain-barrier into the brain vessel of the fetus. Furthermore it may be concluded that the iron carbohydrate complex remains in the brain, i.e. it is not reentering the blood stream.

The data show that the brain iron level in fetuses from a mother that has received 80 mg Fe/kg is close to the control group. Thus, a dosage of 80 mg Fe/kg administered to a mother kept on an iron insufficient diet is adequate for supplementing iron to the fetus brain.

Figure 2:
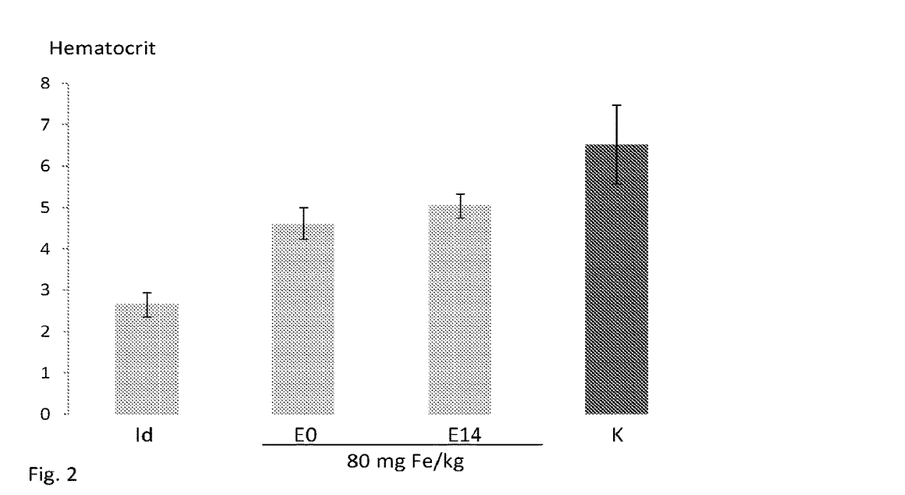
FIG. 2 shows the iron level in the blood (hematokrit) that was measured for the offspring at birth (PO) for the group which received 80 mg Fe/kg. The data is shown in FIG. 2 for the E0 group as well as the E14 group. The data show that the non-treated iron insufficient group (Id) has a significantly lower hematokrit level compared to the E0 and the E14 group, which indicate that the iron carbohydrate complex is biologically processed and converted into red blood cells. The hematokrit levels of the E0 and the E14 group are smaller than the control group (K), which may be explained by the fact that it takes time for the body to produce red blood cells.

The iron level in the blood (hematokrit) was measured for the offspring at birth (P0) for the group which received 80 mg Fe/kg. The data is shown in FIG. 2 for the E0 group as well as the E14 group. The data show that the non-treated iron insufficient group (Id) has a significantly lower hematokrit level compared to the E0 and the E14 group, which indicate that the iron carbohydrate complex is biologically processed and converted into red blood cells. The hematokrit levels of the E0 and the E14 group are smaller than the control group (K), which may be explained by the fact that it takes time for the body to produce red blood cells.

Example 2

Wistar rats aged postnatal (P) days P0 and P70 (adult) were examined. The rats were obtained from timed pregnant rats randomly divided into groups A, B, C, and K (controls) (the day of conception being the E0). For iron deficient studies, the female rats aged postnatal six weeks were fed a low iron diet with an iron content of 5.2 mg Fe/kg (Altromin, Ger) for additionally six weeks. They were then measured for their hematocrit, fertilized and maintained on the iron low diet. For iron-supplementation, the female rats were injected subcutaneously with Iron isomaltoside 1000 (Monofer® obtainable from Pharmacosmos, DK) at a dose of 80 mg Fe/kg on day E0 (group A), E14 (group B), or the day of giving birth equaling day P0 (group C). From P0, the female rats were transferred to the iron-containing diet with an iron-content of 158 mg Fe/kg (Altromin) and kept on this diet. The rats were kept on their respective diets until P21 at where young male rats were separated from their mother and kept on the same diet until euthanized on P70: The rats were deeply anesthetized with a subcutaneous injection of 0.5 ml/10 g body weight of Hypnorm/Dormicum (Fentanyl/Fluanisone mixed with Midazolam). Subsequently, the chest was opened and blood sampled by heart puncture. The blood was analysed for various hematological parameters with main emphasis on the erythron. The brain stem and liver of the rats were then dissected and used for detection of the concentration of the metals Fe, Cu, and Zn by Inductively Coupled Argon Plasma with Optical Emission Spectrometry detection (ICP-OES) (ICAP 6300 Duo View, Thermo Scientific). The metal content in the various P70 rats were compared with those of P0 rats of either sexes. Additionally, female rats (coming mothers) were euthanized on P42 corresponding to the time for fertilization and their hematocrits and content of Fe, Cu, and Zn measured.

Figure 3A:
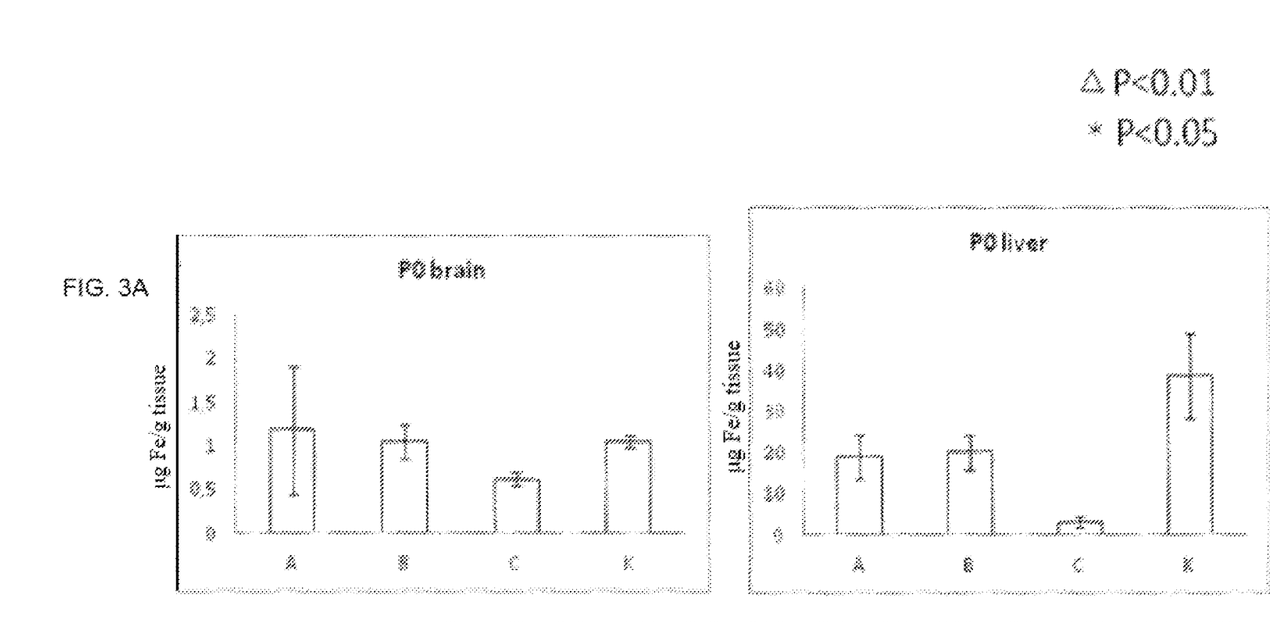
FIG. 3A shows that pups of iron-deficient mothers that did not receive iron therapy during pregnancy (C) had a significant, one third lower iron-level in the brain at P0 than pups of the control mothers (K). In contrast, pups of iron-deficient females that received Iron isomaltoside 1000 (Monofer® obtainable from Pharmacosmos) at the beginning (A) or two thirds (B) into the pregnancy had normal amounts of brain-iron at birth. Notably, the level of iron in the liver—which represents stored iron—was significantly lower than normal in all 3 test groups: 51% lower in group A, 48% lower in group B, and 92% lower in group C, when compared to the controls (K) at P0.

Pups of iron-deficient mothers that did not receive iron therapy during pregnancy (C) had a significant, one third lower iron-level in the brain at P0 than pups of the control mothers (K) (FIG. 3A). In contrast, pups of iron-deficient females that received Iron isomaltoside 1000 (Monofer® obtainable from Pharmacosmos) at the beginning (A) or two thirds (B) into the pregnancy had normal amounts of brain-iron at birth. Notably, the level of iron in the liver—which represents stored iron—was significantly lower than normal in all 3 test groups: 51% lower in group A, 48% lower in group B, and 92% lower in group C, when compared to the controls (K) at P0.

Figure 3B:
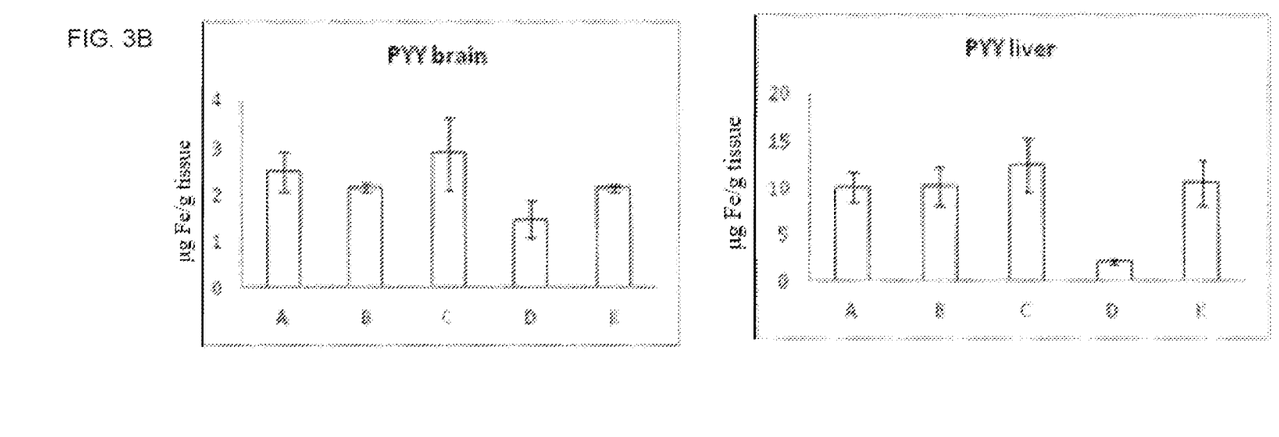
FIG. 3B shows that the pups in groups A, B and C that were given a normal iron diet from P0 to adulthood (P70) and had normal levels of brain-iron when compared to the controls at P70. Pups of the D group, which had only received iron from the breast milk at the time they were weaning (P0 till P21), still had significant one third lower levels of brain-iron compared to the control group. Furthermore, at P70, the level of liver-iron had normalised in the groups A, B and C, whereas their counterparts in group D still had a statistically significant reduction of liver-iron (80%) when compared to controls.

The pups in groups A, B and C were given a normal iron diet from P0 to adulthood (P70) and had normal levels of brain-iron when compared to the controls at P70 (FIG. 3B). Pups of the D group, which had only received iron from the breast milk at the time they were weaning (P0 till P21), still had significant one third lower levels of brain-iron compared to the control group. Furthermore, at P70, the level of liver-iron had normalised in the groups A, B and C, whereas their counterparts in group D still had a statistically significant reduction of liver-iron (80%) when compared to controls.

Figure 4A:
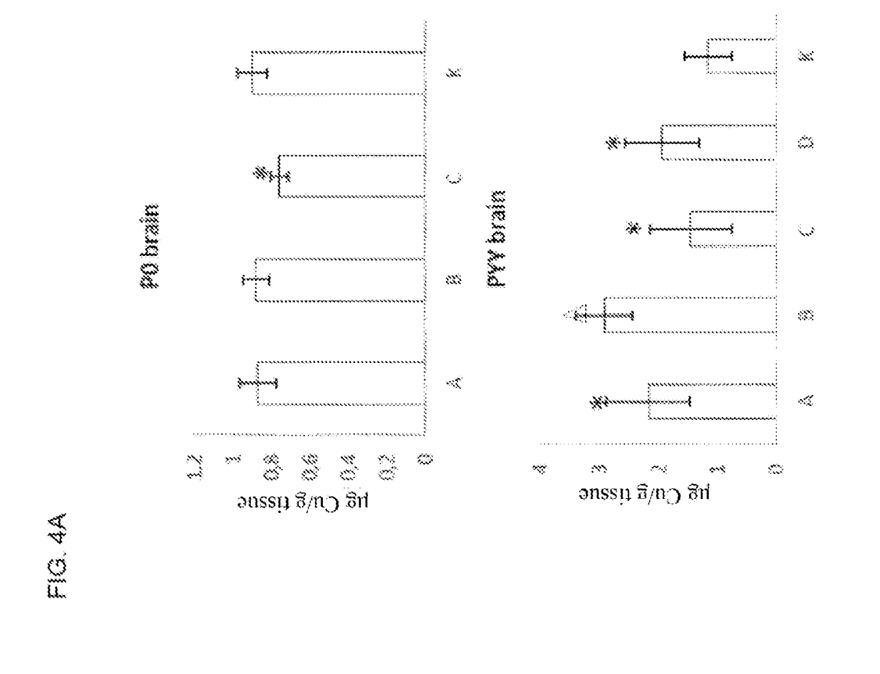
FIG. 4A shows that the amount of copper in the brain was found to be significantly less (16%) in the iron-deficient group C at P0 when compared to controls. The groups that received iron therapy (A and B) had the same levels of brain-copper as the control group at P0. Notably, all test groups except group C had significantly higher amounts of copper in the brain at P70 (increases of A:86%, B:150%, and D: 67% respectively). Group C had a not significant increase of 25%.

The Effects of Iron Deficiency and Iron Therapy on Copper Levels in the Brain and Liver The amount of copper in the brain was found to be significantly less (16%) in the iron-deficient group C at P0 when compared to controls (FIG. 4A). The groups that received iron therapy (A and B) had the same levels of brain-copper as the control group at P0. Notably, all test groups except group C had significantly higher amounts of copper in the brain at P70 (increases of A:86%, B:150%, and D: 67% respectively). Group C had a not significant increase of 25%.

Figure 4B:
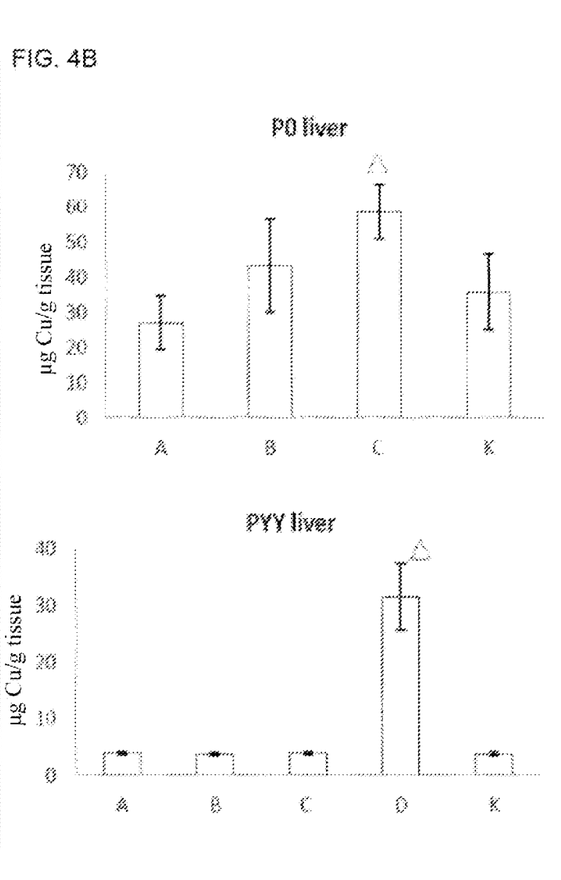
FIG. 4B shows that the level of liver-copper in the iron-deficient group C was found to be significantly higher (63%) than in the controls at P0. The copper levels in groups A and B were not significantly different from the levels in the control group. In the iron-sufficient controls and in the groups that received a normal diet from birth, liver-copper levels dropped by an average of 9 fold from P0 to P70. Interestingly, this drop was much less in the iron-deficient group D where the amount was only halved. This leads to an almost 8 fold difference between the amounts of copper in the liver of the iron-deficient group D and the controls at P70.

The level of liver-copper in the iron-deficient group C was found to be significantly higher (63%) than in the controls at P0 (FIG. 4B). The copper levels in groups A and B were not significantly different from the levels in the control group. In the iron-sufficient controls and in the groups that received a normal diet from birth, liver—copper levels dropped by an average of 9 fold from P0 to P70. Interestingly, this drop was much less in the iron-deficient group D where the amount was only halved. This leads to an almost 8 fold difference between the amounts of copper in the liver of the iron-deficient group D and the controls at P70.

Figure 5:
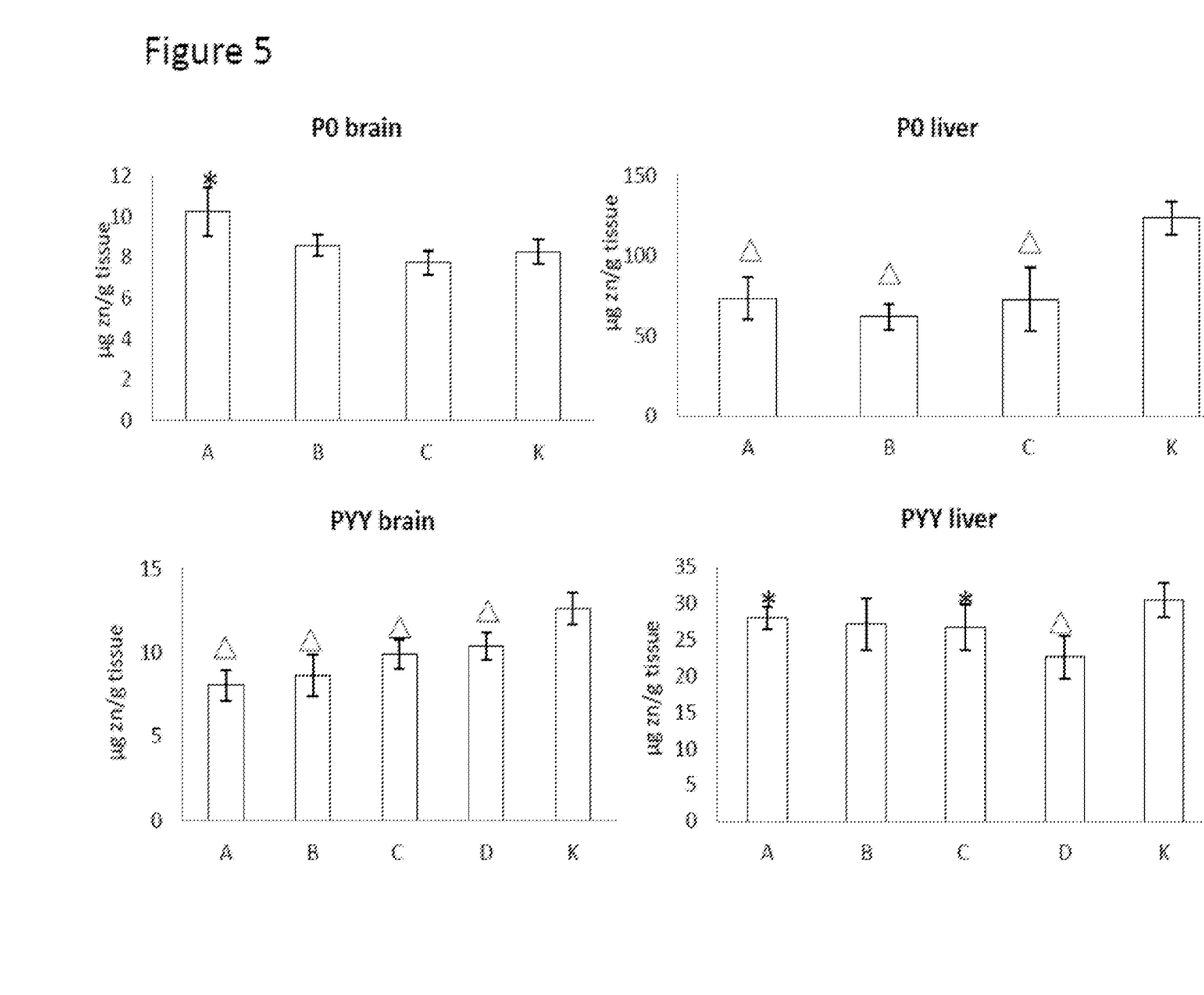
FIG. 5 shows that P0 pups from group A had significantly higher zinc-brain levels (23%) than their counterparts in the control group. The amount of brain-zinc at P0 in groups B and C did not differ from the amount in the controls. In contrast, P70 animals had significantly lower levels of brain-zinc in all test groups when compared to the controls (36%, 32%, 22% and 18% less, respectively, in groups A, B, C, and D). At P70, all test groups—except for the group B—had significantly lower zinc levels in the liver at both P0 and P70 when compared to controls (8%, 12% and 26% less, respectively, for groups A, C and D). The deficiency is most pronounced at P0 and in group D at P70.

The Effects of Iron Deficiency and Iron Therapy on Zinc Levels in the Brain and Liver P0 pups from group A had significantly higher zinc-brain levels (23%) than their counterparts in the control group (FIG. 5). The amount of brain-zinc at P0 in groups B and C did not differ from the amount in the controls. In contrast, P70 animals had significantly lower levels of brain-zinc in all test groups when compared to the controls (36%, 32%, 22% and 18% less, respectively, in groups A, B, C, and D). At P70, all test groups—except for the group B—had significantly lower zinc levels in the liver at both P0 and P70 when compared to controls (8%, 12% and 26% less, respectively, for groups A, C and D). The deficiency is most pronounced at P0 and in group D at P70.

The results we present above show that iron deficiency in pregnant mothers affect iron levels in new born pups. The fetal iron deficiency further affects the metabolism of copper and zinc. Our data indicates that some damaging effect of fetal iron deficiency on brain copper and brain zinc metabolism persist into adult life irrespective of normalised iron, copper and zinc levels in early prenatal or postnatal life. Interestingly, the metabolism of copper and zinc in the brain of adult offspring is affected even when iron deficient mothers receive iron therapy on the day of mating. This indicates that iron deficiency even prior to pregnancy affects parameters of metal metabolism in the progeny. This suggests that normal iron levels should preferably be secured even before pregnancy in order to minimize disturbances in the metabolism in the brain and body of the offspring throughout life.

We show that Iron isomaltoside 1000 (Monofer®) is capable of crossing both the blood-placenta barrier and the blood-brain barrier and to reach the brain of the fetus. The brain-iron levels are normal in the newborn pups when iron therapy is administered both at the beginning of pregnancy and two thirds into the pregnancy. However, we still need studies on the effect on brain development in iron-deficient and iron-corrected animals that will elucidate the full potential of iron therapy with Iron isomaltoside 1000 (Monofer®).

Example 3

Iron content in breast milk from mothers treated with a high single-dose infusion of iron isomaltoside 1000 (Monofer®)

The objective was to measure the concentration of iron in maternal milk after treatment with a high single-dose iron isomaltoside 1000 compared to iron content in maternal milk in women treated with standard medical care after postpartum haemorrhage We conducted a sub-study of women included in a single centre parallel randomized open-label trial performed at the Department of Obstetrics, Copenhagen University Hospital—Rigshospitalet. Healthy women with a singleton delivery and postpartum haemorrhage exceeding 700 mL within 48 hours after delivery were allocated to either a single dose of 1200 mg iron isomaltoside 1000 or standard medical care. Randomization was carried out by a central computer system. Between February 2014 and September 2014 we collected maternal milk samples from participants three days and one week after inclusion in the trial.

Maternal milk samples were collected from 65 women; 30 participants from the intravenous iron group and 35 participants from the standard medical care group. Mean (±SD) iron content in maternal milk three days after intervention was 72.07±27.36 mg/L and 39.99±17.78 mg/L (P<0.001) in the two groups respectively. One week after intervention the mean iron in maternal milk respectively was 46.75±16.81 mg/L and 44.21±25.23 mg/L (P>0.05).

The results provide information about safety of high single-dose iron isomaltoside 1000 in the lactation period. Treatment with high dose iron isomaltoside 1000 resulted in a transient raise in iron content in maternal milk. The increase disappeared one week after treatment. All measured means of iron in maternal milk were within the normal range of iron content in breast milk.

Example 4

Pharmacokinetic (PK) trials have been carried out with different dosages (100, 200, 250, 500, 1000 mg) of iron isomaltoside 1000 (Monofer®) in four trials. The table 1 below indicates the results obtained.

TABLE 1

|  | Trial 1 Bolus | | Trial 2 Infusion | | Trial 3 Bolus | |
|---|---|---|---|---|---|---|
| PK parameters (unit) | 250 mg (n = 5) | 500 mg (n = 7) | 500 mg (n = 5) | 1000 mg (n = 8) | 100 mg (n = 6) | 200 mg (n = 6) |
| | | | Geometric mean | | | |
| AUC (h × mg/dL) | 16.33 | 19.83 | 23.95 | 35.74 | 8.94 | 20.17 |
| $AUC_{0-t}$ (h × mg/dL) | 12.46 | 14.69 | 18.19 | 22.67 | 10.10 | 23.19 |
| $C_{max}$ (μg/dL) | 274 | 424 | 469 | 553 | 373 | 711 |
| $T_{max}$ (h) | 1.37 | 0.76 | 1.07 | 1.04 | 0.63 | 0.46 |
| $K_e$ (1/h) | 0.0163 | 0.0209 | 0.0185 | 0.0147 | 0.030 | 0.029 |
| $T_½$ (h) | 42.49 | 33 | 37.50 | 47 | 23.2 | 23.5 |

|  | Trial 4 | | Trial 5 | | | Trial 6 | |
|---|---|---|---|---|---|---|---|
|  | Bolus | Infusion | Bolus | | | Bolus | Infusion |
| PK parameters (unit) | 500 mg (n = 8) | 1000 mg (n = 7) | 100 mg (n = 6) | 200 mg (n = 6) | 500 mg (n = 6) | 500 mg (n = 8) | 1000 mg (n = 7) |
| | | | Geometric mean | | | | |
| AUC (h × mg/dL) | 27.05 | 80.31 | 4.03 | 8.54 | 18.61 | 25.34 | 72.49 |
| $AUC_{0-t}$ (h × mg/dL) | 19.17 | 35.96 | 3.00 | 6.26 | 14.34 | 17.16 | 29.96 |
| $C_{max}$ (μg/dL) | 448 | 681 | 99 | 202 | 484 | 536 | 641 |
| $T_{max}$ (h) | 2.12 | 1.66 | 1.00 | 0.91 | 0.57 | 1.13 | 1.53 |
| $K_e$ (1/h) | 0.0200 | 0.0083 | 0.0240 | 0.0226 | 0.0223 | 0.0174 | 0.0079 |
| $T_½$ (h) | 34.64 | 83.08 | 28.86 | 30.72 | 31.14 | 39.87 | 87.87 |

The invention claimed is:

1. A method for treatment or prevention of iron deficiency of a fetus, comprising parenterally administering to the mother of the fetus during pregnancy a pharmaceutical composition comprising an effective amount of an iron carbohydrate complex comprising an iron hydrogenated oligoisomaltoside.

2. The method according to claim 1, wherein the iron deficiency is a brain iron deficiency.

3. The method according to claim 1, comprising treatment or prevention of a disorder caused by brain metal deficiency.

4. The method according to claim 1, wherein the pharmacokinetic half-life ($t_{1/2}$) of the iron carbohydrate complex is 10 hours or more, 12 hours or more, 14 hours, 16 hours, 18 hours, 20 hours, or 22 hours, or more.

5. The method according to claim 1, wherein the total dose of elemental iron from the iron carbohydrate complex administered to the mother is 300 mg elemental iron or more, 400 mg elemental iron or more, 500 mg elemental iron, 600 mg elemental iron, 700 mg elemental iron, 800 mg elemental iron, 900 mg elemental iron, 1000 mg elemental iron, or more.

6. The method according to claim 1, wherein the iron carbohydrate complex comprises a carbohydrate component comprising a backbone of glucose units linked by α-1,6 glycosidic linkages and optionally branches of glucose units linked to the backbone through α-1,3 glycosidic linkages, wherein the proportion of α-1,3 glycosidic linkages to α-1,6 glycosidic linkages is less than 5:100, or is less than 1:100, or wherein the carbohydrate component does not comprise detectable branches of glucose units linked by α-1,3 glycosidic linkages to the backbone.

7. The method according to claim 1, wherein the iron carbohydrate complex is (1→6)-α-D-glucopyranan-(1→6)-D-glucitol iron(III) complex.

8. The method according to claim 1, wherein the weight average molecular weight (MW) of the carbohydrate component of the iron carbohydrate complex is 800 to 2,000 Daltons or is about 1,000 Daltons.

9. The method according to claim 1, wherein the apparent molecular weight of the iron carbohydrate complex measured relative to dextran standards, is 400,000 Daltons or less, is 300,000 Daltons or less, or is 200,000 Daltons or less.

10. The method according to claim 1, wherein the pharmaceutical composition is infused into the mother during a 3 to 30 minute time period, during a 16 to 30 minute time period, during a 5 to 25 minute time period, or during a 10 to 20 minute time period.

11. The method according to claim 1, wherein the iron carbohydrate complex is administered to the mother during the first trimester of pregnancy, during the second trimester of pregnancy, or during the third trimester of pregnancy.

12. The method according to claim 1, wherein the mother is subjected to a further administration of the iron carbohydrate complex during pregnancy or the breastfeeding period, and/or wherein a further administration of the iron carbohydrate complex is performed 1 month to 12 months after the previous administration.

13. The method according to claim 1, wherein the administration of the iron carbohydrate complex prevents or treats abnormal development of the fetal brain or wherein the administration of the iron carbohydrate complex prevents or treats abnormal development of the fetal substantia nigra, thalamus, putamen, ventral midbrain, or pallidum.

14. The method according to claim 1, wherein the iron carbohydrate complex administered to the mother supports cognitive, motor, social-emotional, or neurophysiologic development of the fetus.

15. The method according to claim 3, wherein the disorder is caused by brain iron deficiency, resulting in copper or zinc imbalance.

16. The method according to claim 3, wherein the disorder caused by brain metal deficiency is at least one of restless leg syndrome (RLS), attention deficit hyperactivity disorder (ADHD), attention deficit disorder (ADD), absence seizure, bipolar disorder, schizophrenia, obsessive-compulsive disorder (OCD), autism, borderline personality disorder (BPD), Alzheimer's disease and Parkinson's disease.

17. The method according to claim 1, wherein the maximum concentration of serum total iron ($C_{max}$) after administering the pharmaceutical composition is between 99 µg/dl and 681 µg/dl.

18. A method for treatment or prevention of iron deficiency of an infant, comprising parenterally administering to the mother of the infant during breastfeeding an effective amount of a pharmaceutical composition comprising an iron carbohydrate complex to increase the concentration of iron in the maternal milk, wherein the iron carbohydrate complex comprises an iron hydrogenated oligoisomaltoside.

19. The method according to claim 1, wherein the iron carbohydrate complex is iron isomaltoside 1000.

20. The method according to claim 1, wherein:
the iron carbohydrate complex is iron isomaltoside 1000;
the pharmaceutical composition is intravenously infused into the mother for 20to 30 min; and
wherein the dose of elemental iron from the iron carbohydrate complex administered to the mother is 800 mg elemental iron or more, or is 1000 mg elemental iron.

21. The method according to claim 18, wherein the iron carbohydrate complex is iron isomaltoside 1000.

22. The method according to claim 18, wherein:
the iron carbohydrate complex is iron isomaltoside 1000;
the pharmaceutical composition is intravenously infused into the mother for 20to 30 min; and
wherein the dose of elemental iron from the iron carbohydrate complex administered to the mother is 800 mg elemental iron or more, or is 1000 mg elemental iron.

* * * * *